United States Patent
Hoshino

(10) Patent No.: US 9,322,825 B2
(45) Date of Patent: Apr. 26, 2016

(54) MODIFIED ANTI-HEPARIN/PF4 COMPLEX ANTIBODY AND HIT ANTIBODY STANDARD

(75) Inventor: Nobuhiro Hoshino, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 1194 days.

(21) Appl. No.: 13/061,072

(22) PCT Filed: Aug. 26, 2009

(86) PCT No.: PCT/JP2009/064828
§ 371 (c)(1), (2), (4) Date: Feb. 25, 2011

(87) PCT Pub. No.: WO2010/024271
PCT Pub. Date: Mar. 4, 2010

(65) Prior Publication Data
US 2011/0171753 A1    Jul. 14, 2011

(30) Foreign Application Priority Data
Aug. 27, 2008    (JP) ................................ 2008-218801

(51) Int. Cl.
*G01N 33/564* (2006.01)
*C07K 16/18* (2006.01)
*C07K 16/24* (2006.01)
*G01N 33/531* (2006.01)
*C07K 16/36* (2006.01)
*C07K 16/44* (2006.01)

(52) U.S. Cl.
CPC .............. *G01N 33/564* (2013.01); *C07K 16/18* (2013.01); *C07K 16/24* (2013.01); *C07K 16/36* (2013.01); *C07K 16/44* (2013.01); *G01N 33/531* (2013.01); *C07K 2317/21* (2013.01); *C07K 2317/32* (2013.01); *G01N 2800/222* (2013.01)

(58) Field of Classification Search
None
See application file for complete search history.

(56) References Cited

U.S. PATENT DOCUMENTS

| | | | |
|---|---|---|---|
| 4,929,543 A * | 5/1990 | Kientsch-Engel et al. | ....... 435/5 |
| 5,466,582 A | 11/1995 | Amiral | |
| 5,478,753 A † | 12/1995 | Wong | |
| 5,480,792 A | 1/1996 | Buechler et al. | |
| 5,972,717 A | 10/1999 | Aster et al. | |
| 5,972,718 A | 10/1999 | Moghaddam et al. | |
| 6,939,678 B1 * | 9/2005 | Buechler et al. | ............... 435/7.1 |
| 6,964,854 B1 | 11/2005 | Arepally et al. | |
| 7,011,953 B2 | 3/2006 | Abdelouahed et al. | |
| 2006/0040323 A1 | 2/2006 | Arepally et al. | |
| 2006/0172438 A1 | 8/2006 | Milunic et al. | |
| 2007/0190582 A1 | 8/2007 | Poncz et al. | |
| 2010/0009389 A1 † | 1/2010 | Khan | |

FOREIGN PATENT DOCUMENTS

EP    0 636 886 B1    8/2000

OTHER PUBLICATIONS

Muller, Stefan; Communication from Applicant's representative dated May 14, 2014 as filed in European Patent Office in counterpart application EP 09809922.9, 8 pages, retrieved from https://register.epo.org/application?number=EP09809922&lng=en&tab=doclist on Jan. 30, 2015.*

Harlow & Lane, "Antibodies: A Laboratory Manual" (1988) Cold Spring Harbor Laboratory Press, Cold Spring Harbor, New York, pp. 25-26.*

Hackett, Jr., J. et al., "Recombinant Mouse-Human Chimeric Antibodies as Calibrators in Immunoassays That Measure Antibodies to *Toxoplasma gondii*," *J. Clin. Microbiol.*, May 1998, p. 1277-1284, vol. 36, No. 5. —.

Ichikawa, K. et al., "A Chimeric Antibody with the Human γI Constant Region as a Putative Standard for Assays to Detect IgG β$_2$-Glycoprotein I-Dependent Anticardiolipin and Anti-β$_2$-Glycoprotein I Antibodies," *Arthritis & Rheumatism*, vol. 42, No. 11, Nov. 1999, pp. 2461-2470.

Jones, M.L. and Barnard, R.T., "Use of Chimeric Antibodies as Positive Controls in an Enzyme-Linked Immunosorbent Assay for Diagnosis of Scrub Typhus (Infection by *Orientia tsutsugamushi*)," *Clin. Vaccine Immunol.*, Oct. 2007, p. 1307-13 10, vol. 14; No. 10.

Platelet Factor 4 Complexed to Heparin Is the Target for Antibodies Generated in Heparin-Induced Thrombocytopenia; *Thrombosis and Haemostasis*; 1992; pp. 95-96; vol. 68, No. 1; Germany, Amiral et al.

A. Greinacher et al.; Heparin-Associated Thrombocytopenia: Isolation of the Antibody and Characterization of a Multimolecular PF4-Heparin Complex as the Major Antigen; *Thrombosis and Haemostasis*; 1994; pp. 247-251; vol. 71, No. 2; Germany.

J. Amiral et al; Antibodies to Macromolecular Platelet Factor 4-Heparin Complexes in Heparin-induced Thrombocytopenia: a Study of 44 Cases; *Thrombosis and Haemostasis*; 1995; pp. 21-28; vol. 73, No. 1; Germany.

G. M. Arepally et al.; Characterization of a murine monoclonal antibody that mimics heparin-induced thrombocytopenia antibodies; *Blood*; 2000; pp. 1533-1540; vol. 95, No. 5.

A. Barone et al.; The Expression in *Escherichia coli* of Recombinant Human Platelet Factor 4, a Protein with Immunoregulatory Activity; *Journal of Biological Chemistry*; 1988; pp. 8710-8715; vol. 263, No. 18.

(Continued)

*Primary Examiner* — Christine Foster
(74) *Attorney, Agent, or Firm* — Kilpatrick Townsend & Stockton LLP

(57) ABSTRACT

Provided is a modified antibody which enables the quantitative measurement of the amount of a heparin/PF4 complex, an onset factor of heparin-induced trombocytopenia (HIT), without the influence of the presence of PF4, and which can be used as an HIT antibody standard specific for the heparin/PF4 complex. The modified antibody is prepared by linking a human IgG, or an antibody fragment derived from a human IgG, to a monoclonal antibody obtained by immunizing an animal (excluding a human) with the heparin/PF4 complex.

5 Claims, 6 Drawing Sheets

(56) References Cited

OTHER PUBLICATIONS

G. P. Visentin et al.; Antibodies from Patients with Heparin-induced Thrombocytopenia/Thrombosis Are Specific for Platelet Factor 4 Complexed with Heparin or Bound to Endothelial Cells; *J. Clin. Invest.*; 1994; pp. 81-88; vol. 93.

T. Warkentin et al.; Testing for Heparin-Induced Thrombocytopenia Antibodies; *Transfusion Medicine Reviews*; 2006; pp. 259-272; vol. 20, No. 4.

Trossaert et al., "High incidence of anti-heparin/platelet factor 4 antibodies after cardiopulmonary bypass surgery," British Journal of Haematology, Jun. 1998, vol. 101, No. 4, pp. 653-655.

Supplementary European Search Report, Nov. 7, 2012, EP application No. 09 80 9922, 4 pages.

HemaCare Bioscience, Certificate of Analysis: Toxoplasma IgM Positive Control (Chimeric), Ft. Lauderdale, FL 33309; cited in EP Communication Pursuant to Rule 114(2)EPC on Jul. 19, 2012, (one page).

Non-final Office Action from the U.S. Pat. No. 20100009389, mailing date of the Office Action Nov. 9, 2011.†

Final Office Action from the U.S. Pat. No. 20100009389, mailing date of the Office Action May 31, 2012.†

Non-final Office Action from the U.S. Appl. No. 12/502,814; Mailing date of the Office Action Nov. 9, 2011 (pp. 1-7).†

\* cited by examiner
† cited by third party

Human-IgG-linked monoclonal antibody (5A1)

Human-IgG-Fc-fraction-linked monoclonal antibody (5A1)

Human-IgG-Fc-fraction-linked monoclonal antibody (2D6B)

Human-IgG-Fc-fraction-linked monoclonal antibody (10E6)

Anti-heparin/PF4 mouse monoclonal antibody (5A1)

Anti-heparin/PF4 mouse monoclonal antibody (2D6B)

Anti-heparin/PF4 mouse monoclonal antibody (10E6)

MODIFIED ANTI-HEPARIN/PF4 COMPLEX ANTIBODY AND HIT ANTIBODY STANDARD

TECHNICAL FIELD

The present invention relates to a modified anti-heparin/PF4 complex antibody that reacts with a heparin/PF4 complex, but does not react with PF4. The modified antibody of the present invention enables the measurement of the heparin/PF4 complex, without the influence of the presence of PF4, and can be used as an HIT (heparin-induced trombocytopenia) antibody standard which can be constantly supplied and which is used for measuring an HIT antibody in the test of HIT. Therefore, the present invention further relates to the HIT antibody standard, a process of preparing the HIT antibody standard, a method of quantitatively measuring an HIT antibody using the HIT antibody standard, and a kit for measuring an HIT antibody comprising the HIT antibody standard.

BACKGROUND ART

Heparin, which is an anticoagulant, is used to avoid blood coagulation during the treatment of thromboembolism or disseminated intravascular coagulation (DIC), dialysis, or extracorporeal circulation.

However, it is known that the administration of heparin sometimes causes HIT (heparin-induced trombocytopenia), and the responsible factor is considered to be the generation of an autoantibody (HIT antibody) against platelet factor 4 (PF4) to which heparin binds. The diagnosis of HIT is carried out by measuring the production of the HIT antibody. More particularly, the HIT antibody strongly reacts with heparin/PF4, but hardly reacts with PF4, and therefore, an ELISA (Enzyme-Linked ImmunoSorbent Assay) method in which a human plasma sample is reacted with a heparin/PF4 complex immobilized on a plate, followed by an enzyme-labeled anti-human-immunoglobulin antibody, and an enzyme reaction is carried out to determine the presence or absence of the HIT antibody is known (Non-patent references 1 to 3).

However, the HIT antibody contained in samples is merely qualitatively or semi-quantitatively measured by absorbance (OD value) in these references.

CITATION LIST

Non-Patent Literature

[Non-patent literature 1] Thrombosis and Haemostasis, Germany, 1992, vol. 68, no. 1, p. 95-96
[Non-patent literature 2] Thrombosis and Haemostasis, Germany, 1994, vol. 71, no. 2, p. 247-251
[Non-patent literature 3] Thrombosis and Haemostasis, Germany, 1995, vol. 73, no. 1, p. 21-28

SUMMARY OF INVENTION

Technical Problem

The present inventor considered that it was important for the enhancement of the treatment efficacy of HIT to quantitatively measure the HIT antibody contained in a sample. The present inventor further considered that it was important to quantitatively measure the amount of the heparin/PF4 complex, an onset factor of HIT, without the influence of the presence of PF4.

More particularly, the quantitative measurement of the HIT antibody contained in a sample needs a standard substance having reactivities similar to those of the HIT antibody. However, because the HIT antibody is an autoantibody produced in a human, either of (1) an HIT antibody extracted from human subjects (HIT patients), or (2) an anti-heparin/PF4 complex antibody obtained by immunizing an animal with the heparin/PF4 complex (utilizing crossreactivity to human immunoglobulins) was merely used as the standard substance for the measuring reagent. With respect to (1), because human (HIT patients) material is used, several problems such as ethical constraints, quantitative limits, and quality assurance are raised, and thus, the practical use is impossible. With respect to (2), the antibodies obtained by immunizing an animal with the antigen usually reacted with both the heparin/PF4 complex and PF4, that is to say, these antibodies were not standards specific for the heparin/PF4 complex. In this regard, there is a reference (G. M. Arepally et al., Blood, 95(5), 1533-1540, 2000) reporting that a mouse monoclonal antibody which weakly bound to PF4 and strongly bound to the heparin/PF4 complex was obtained, but there was a little possibility to obtain this monoclonal antibody, and thus, not every supplier could obtain it. Further, in the case of (2), it is considered that there is sometimes no correlation to samples, because the measurement is carried out using crossreactivity to human immunoglobulins.

The present inventor has conducted intensive studies to solve the above-mentioned problems, and found that a modified antibody which does not react with PF4, but reacts with the heparin/PF4 complex can be easily prepared by using an antibody obtained by immunizing an animal with the heparin/PF4 antibody which is relatively easily available, and that the modified antibody can be used as an HIT antibody standard specific for the heparin/PF4 complex.

An object of the present invention is to provide a modified antibody which does not react with PF4, but reacts with the heparin/PF4 complex and which can be used as an HIT antibody standard specific for the heparin/PF4 complex.

Solution to Problem

The inventor immunized a mouse with the heparin/PF4 complex, and used myeloma cells prepared from spleen cells of the mouse to obtain mouse monoclonal antibodies in accordance with a conventional method. These mouse monoclonal antibodies reacted with the heparin/PF4 complex, but also reacted with PF4 alone with a reactivity of about 80%. Next, human IgG or its Fc fraction (IgG-Fc fraction) was linked to each of the mouse monoclonal antibodies using a crosslinking agent, and the reactivity thereof against PF4 or the heparin/PF4 complex was examined. As a result, it was unexpectedly found that the reactivity against PF4 alone was remarkably decreased, while the reactivity against the heparin/PF4 complex was maintained. From these findings, the inventor found that a human-IgG-linked anti-heparin/PF4 mouse monoclonal antibody or a human-IgG-Fc-fraction-linked anti-heparin/PF4 mouse monoclonal antibody can be used as an HIT antibody standard, which has similar reactivities to the anti-heparin/PF4 human antibody (HIT antibody) and which may be used in quantitatively measuring the HIT antibody, and completed the present invention. The present invention provides the following (1) to (6).

(1) A modified anti-heparin/PF4 complex antibody, characterized in that a human IgG or an antibody fragment derived from a human IgG is linked to a monoclonal antibody obtained by immunizing an animal (excluding a human) with a heparin/PF4 complex.

(2) The modified anti-heparin/PF4 complex antibody of (1), which reacts with the heparin/PF4 complex, but does not react with PF4.
(3) An HIT antibody standard, characterized in that a human IgG or an antibody fragment derived from a human IgG is linked to a monoclonal antibody obtained by immunizing an animal (excluding a human) with a heparin/PF4 complex.
(4) A process of preparing an HIT antibody standard, characterized by linking a human IgG or an antibody fragment derived from a human IgG to a monoclonal antibody obtained by immunizing an animal (excluding a human) with a heparin/PF4 complex.
(5) A method of quantitatively measuring an HIT antibody contained in a sample, characterized by using the HIT antibody standard of (3).
(6) A kit for measuring an HIT antibody, characterized by comprising the HIT antibody standard of (3).

The term "HIT antibody" as used herein means an autoantibody which is produced in a human, and which strongly reacts with the heparin/PF4 complex, but hardly reacts with PF4 alone.

The term "anti-heparin/PF4 complex antibody" is used to mean an antibody which reacts with the heparin/PF4 complex, regardless of its origin or the reactivity to PF4 alone, unless otherwise specified. More particularly, the "anti-heparin/PF4 complex antibodies" include, for example, an antibody which reacts with PF4 alone, an antibody which does not react with PF4 alone, an autoantibody produced in a human (for example, the HIT antibody), and an antibody obtained by immunizing an animal excluding a human, so long as they react with the heparin/PF4 complex.

Advantageous Effects of Invention

According to the present invention, a modified antibody which does not react with PF4 alone, but reacts with the heparin/PF4 complex is provided. Further, an HIT antibody standard which is easily available and consistently shows a good repeatability, and a process of preparing the HIT antibody standard, are provided. Furthermore, a method of quantitatively measuring an HIT antibody using the HIT antibody standard, and a kit for quantitatively measuring the HIT antibody, are provided.

Figure 1:
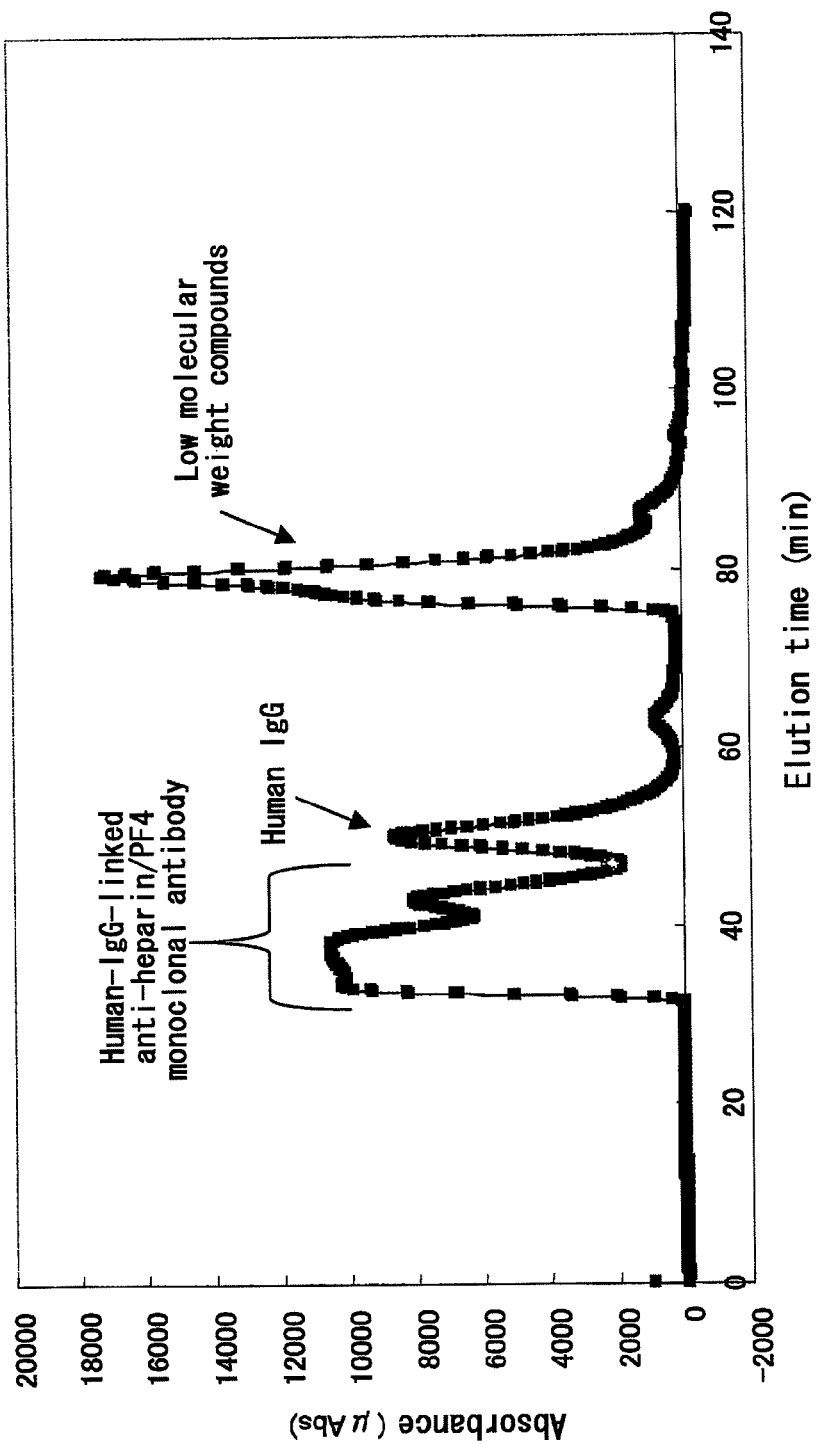
FIG. 1 is a chromatogram showing the fractionation pattern of a human-IgG-linked anti-heparin/PF4 mouse monoclonal antibody by gel filtration HPLC.

DESCRIPTION OF EMBODIMENTS (1) Preparation of Heparin/PF4 Complex

Platelet factor 4 (PF4) is a protein having a molecular weight of 31,000, which is a tetramer composed of four subunits each having a molecular weight of 7,800. Heparin and PF4 form complexes at various ratios in vivo, but a complex composed of two molecules of PF4 and a molecule of heparin is considered the optimum ratio, because the electric charge is neutralized. The heparin/PF4 complex used in preparing the modified antibody of the present invention may be prepared by mixing heparin with PF4 purified from human platelets, or in accordance with known methods such as a known recombinant protein preparation method or a fusion protein expression method as described in Example 1 below. In this regard, the type of heparin or a partial modification in the amino acid sequence of PF4 is not limited, so long as such a recombinant or fusion protein has properties similar to those of heparin/PF4 complexes present in vivo. The properties similar to those of heparin/PF4 complexes present in vivo mean, for example, that an HIT antibody produced in a HIT patient shows a similar reactivity against the prepared heparin/PF4 complex to the reactivity shown against heparin/PF4 complexes present in vivo.

PF4 may be prepared using a known recombinant protein preparation method, and a host may be appropriately selected from, for example, E. coli, yeast, insect cells, a silkworm larva, and animal cells.

Heparin used may be appropriately selected from, for example, unfractionated heparin, a high-molecular-weight fraction of heparin, and a low-molecular-weight fraction of heparin.

(2) Preparation of Anti-Heparin/PF4 Complex Monoclonal Antibody

An anti-heparin/PF4 complex monoclonal antibody which may be used in the present invention may be obtained by, for example, a monoclonal antibody production method using a hybridoma prepared by a known cell fusion method. An antibody producing cell may be selected from animals other than a human, for example, a mouse, a rat, or a guinea pig. More particularly, a heparin/PF4 complex is used as an antigen, and a screening is carried out using this heparin/PF4 complex to prepare a hybridoma producing a monoclonal antibody which may be used in the present invention. The monoclonal antibody of interest may be prepared from the obtained hybridoma. Hybridomas and monoclonal antibodies may be prepared in accordance with conventional methods, as described in, for example, Zoku Seikagku Jikken Koza, edited by the Japanese Biochemical Society, or Meneki Seikagaku Kenkyu Ho, edited by the Japanese Biochemical Society.

The desired monoclonal antibody may be prepared by cultivating hybridoma cells (for example, mouse hybridoma) producing the monoclonal antibody, for example, in an appropriate medium or in the abdominal cavity of a mammal such as a mouse. Hybridomas may be generally prepared by, for example, cell-fusing spleen cells from a mammal such as a mouse or a bird immunized with a heparin/PF4 complex, with myeloma cells from a mammal such as a mouse, in accordance with the method described in Nature, vol. 256, p. 495 (1975). More particularly, the preparation may be carried out in accordance with the methods described in Examples below.

The medium which may be used in cultivating the hybridoma is not limited, so long as it is suitable for the cultivation of hybridomas. Preferably, a Dulbecco's modified Eagle's minimum essential medium (hereinafter referred to as DME) supplemented with fetal calf serum, L glutamine, L-pyruvate, and antibiotics (penicillin G and streptomycin) may be used. In the case that the cultivation is carried out in a medium, the hybridoma is cultivated, for example, at 37° C. in 5% $CO_2$ for about 3 days. In the case that the cultivation is carried out in the abdominal cavity of a mouse, the hybridoma is cultivated, for example, for about 14 days.

The monoclonal antibody of interest can be separated and purified from the above-prepared culture broth or ascites from a mammal by, for example, a commonly-used method for the isolation and purification of proteins. Examples of the method include salting-out with ammonium sulfate, ion-exchange chromatography using ion-exchange cellulose, molecular sieve column chromatography using a molecular sieve gel, affinity column chromatography using protein A binding polysaccharides, dialysis, and lyophilization.

The "anti-heparin/PF4 complex monoclonal antibody" which may be used in the present invention includes an antibody fragment. The antibody fragment is a fragment which is derived from the desired monoclonal antibody, and which has the same reactivity as that of the original monoclonal antibody. Examples of the antibody fragment of the present invention include Fab, Fab', $F(ab')_2$, and Fv. These antibody fragments may be obtained, for example, by digesting the original monoclonal antibody with a protease in accordance with a conventional method and carrying out a conventional method for the separation and purification of proteins.

(3) Preparation of Human-IgG-Linked Anti-Heparin/PF4 Complex Monoclonal Antibody and Human-IgG-Derived Antibody-Fragment-Linked Anti-Heparin/PF4 Complex Monoclonal Antibody Human IgG used in the present invention may be purchased from AbD Serotec or the like. An antibody fragment derived from human IgG may be purchased from BETHYL or the like, or may be prepared in a similar fashion to that described with respect to the antibody fragment in the above section (2). Human IgG may be purified from a human serum by a known method.

The human-IgG-derived antibody fragment used in the present invention may be selected, regardless of whether or not it has the same reactivity as that of the original human IgG. The antibody fragment may be, for example, Fab, Fab', $F(ab')_2$, Fc, or Fv.

The human IgG component which may be used in the present invention and which is linked to the anti-heparin/PF4 complex monoclonal antibody may be appropriately selected from the whole of human IgG, and antibody fragments (Fab, Fab', $F(ab')_2$, Fc, Fv, or the like) derived from human IgG, preferably the whole of human IgG, an Fc fraction derived from human IgG, or an Fab fraction derived from human IgG. The Fc fraction derived from human IgG is sometimes herein referred to as the human IgG-Fc fraction.

The linkage of human IgG or a human-IgG-derived antibody fragment to an anti-heparin/PF4 complex monoclonal antibody may be carried out by appropriately selecting a binding method and binding conditions in accordance with a conventional method, so long as it is a method for linking proteins to each other. For example, a crosslinking agent to modify proteins may be used. Examples of the crosslinking agent include disuccinimidyl glutarate having succinimide groups at both ends, or its analogues; bismaleimide triethyleneglycol having maleimide groups at both ends, its analogues; maleimidecaproyl oxysuccinimide ester having both groups at the ends, or its analogues; or glutaraldehyde.

(4) Evaluation of Modified Antibody or Hit Antibody Standard

With respect to the above-prepared modified antibodies (for example, human-IgG-linked anti-heparin/PF4 complex monoclonal antibody or human-IgG-derived antibody-fragment-linked anti-heparin/PF4 complex monoclonal antibody), a confirmation that it reacts with the heparin/PF4 complex, but does not react with PF4, or an evaluation whether or not it can be used as an HIT antibody standard, may be carried out by measuring its reactivity against the heparin/PF4 complex and its reactivity against PF4, and examining whether or not it shows the same reactivities as those of an HIT antibody present in vivo. For example, in accordance with the methods described in Examples 5 and 6, a heparin/PF4 complex plate and a PF4 plate are prepared, and the reactivity of the human-IgG-linked anti-heparin/PF4 complex monoclonal antibody or human-IgG-derived antibody-fragment-linked anti-heparin/PF4 complex monoclonal antibody against each of these plates is determined. When the original anti-heparin/PF4 complex monoclonal antibody, which shows the same reactivities against both plates, is linked to human IgG, or a human-IgG-derived antibody fragment, it is examined whether or not its reactivity against the heparin/PF4 complex plate is maintained, but its reactivity against the PF4 plate is remarkably decreased, i.e., it shows a low reactivity similar to that of the HIT antibody present in vivo.

Further, the prepared human-IgG-linked anti-heparin/PF4 complex monoclonal antibody or human-IgG-derived antibody-fragment-linked anti-heparin/PF4 complex monoclonal antibody is diluted to prepare samples having different concentrations, and it is examined whether or not a standard curve can be drawn. Such a standard curve can be prepared using a known method, for example, in accordance with a tertiary approximation of Microsoft Excel, a spline approximation, or the like.

Appropriate modified antibodies selected using the above examinations can be used as the modified antibody or the HIT antibody standard of the present invention.

(5) Method of Quantitatively Measuring Hit Antibody in Sample Using Hit Antibody Standard As a method of quantitatively measuring an HIT antibody contained in a sample, a known immunological measuring method may be used. Examples of the immunological measuring method include an ELISA method, an RIA method, immunoagglutination, and immunochromatography.

The ELISA method may be carried out as follows. The heparin/PF4 complex is immobilized on an insoluble carrier. The immobilized heparin/PF4 complex is brought into contact with a sample to be assayed, or a set of dilutions having different concentrations prepared from the HIT antibody standard of the present invention, followed by an antibody for detection prepared by conjugating an anti-human-immunoglobulin antibody or its antibody fragment with a label. A signal from the label of the antibody for detection, which binds to the immobilized heparin/PF4 complex, via an HIT antibody contained in the sample, can be detected. Next, a standard curve is drawn based on the measured values for the dilutions having different concentrations prepared from the HIT antibody standard of the present invention. The standard curve and the measured value of the sample are used to determine the concentration of the HIT antibody contained in the sample.

The immunoagglutination may be carried out as follows. The heparin/PF4 complex, and an anti-human-immunoglobulin antibody or its antibody fragment are separately immobilized on an insoluble carrier. The immobilized heparin/PF4 complex or the immobilized anti-human-immunoglobulin antibody or its antibody fragment is brought into contact with a sample to be assayed, or a set of dilutions having different concentrations prepared from the HIT antibody standard of the present invention. Agglutination with the HIT antibody contained in the sample is carried out, and the degree of the agglutination can be detected. Next, a standard curve is drawn based on the measured values for the dilutions having different concentrations prepared from the HIT antibody standard of the present invention. The standard curve and the measured value of the sample are used to determine the concentration of the HIT antibody contained in the sample.

The standard curve on the basis of the HIT antibody standard may be drawn, simultaneously with the measurement of the sample, or separately from the measurement and may be referred to.

As described above, the HIT antibody standard of the present invention may be used to carry out the method of the present invention for quantitatively measuring an HIT antibody in a sample. Samples which may be assayed by the method of the present invention for quantitatively measuring an HIT antibody are not particularly limited, so long as it is the HIT antigen standard of the present invention of which the concentration is known, or a sample suspected of containing an HIT antibody. Examples of the sample include biological specimens, such as blood, plasma, serum, and urine, preferably plasma or serum.

The insoluble carrier which may be used in the immunological analysis method of the present invention utilizing an ELISA method is not particularly limited. Examples of the insoluble carrier include polymers (for example, polyethylene, polystyrene, polypropylene, polyvinyl chloride, polyester, polyacrylonitrile, fluorine resins, crosslinked dextran, and polysaccharides), nitrocellulose, papers, and agarose, and combinations thereof.

As a labeling substance, an enzyme, a fluorescent substance, or a luminescent substance may be used. Examples of the enzyme include alkaline phosphatase, peroxidase, and 3-D-galactosidase. Examples of the fluorescent substance include fluorescein isothiocyanate. Examples of the luminescent substance include acridinium esters and luciferin.

The insoluble carrier which may be used in the immunological analysis method of the present invention utilizing an agglutination reaction may be any insoluble carrier which is generally used in a immunological analysis method utilizing the agglutination reaction of antigen-antibody reaction, such as latex particles (in particular, polystyrene latex particle). A monoclonal antibody may be immobilized on the insoluble carrier by a known method, such as a chemical binding method (using carbodiimide glutaraldehyde, or the like as a crosslinking agent) or physical adsorption. A complex of a monoclonal antibody and the insoluble carrier (antibody/carrier complex) may be formed as described above, and may be used in the immunological analysis method of the present invention.

Because the HIT antibody is an onset factor of HIT (heparin-induced trombocytopenia), the amount of the HIT antibody contained in a sample may be measured using the method of the present invention for quantitatively measuring an HIT antibody, and the presence or absence of HIT and/or the degree of HIT may be detected.

To conveniently carry out the present invention, a reagent kit containing the HIT antibody standard and the heparin/PF4 complex may be preferably used. The HIT antibody standard may be previously adjusted to an optimum concentration, or may be appropriately prepared when used. An insoluble carrier on which the heparin/PF4 complex is to be immobilized, or an insoluble carrier on which the heparin/PF4 complex is previously immobilized may be added to the kit. A labeled anti-human-immunoglobulin antibody for detection, or a labeled anti-human-immunoglobulin antibody fragment may be added to the kit. Preparations and the use of the kit may be carried out in accordance with a manual attached to the kit.

EXAMPLES

The present invention now will be further illustrated by, but is by no means limited to, the following Examples.

Example 1

Preparation of Heparin/PF4 Complex

Recombinant platelet factor 4 (PF4) was prepared in accordance with the following procedure.

An gene encoding the amino acid sequence of amino acids 32-101 of human platelet factor 4 [NCBI (National Center for Biotechnology Information) Accession No. P02776] was chemically synthesized by a PCR method. To carry out a direct expression in an *E. coli* expression system, a GST-PF4 expression vector for expressing PF4 having GST (glutathione S-transferase) and a PSP (PreScission Protease) cleavage sequence at the N-terminus was constructed. An *E. coli* host BL21 (DE3) was transformed with this expression vector, and the culture conditions were examined.

The yield of GST-PF4 purified by an affinity chromatography with a Glutathione Sepharose 4B was approximately 20 mg per 1 L of the culture (corresponding to approximately 5 mg of PF4; measured by SDS-PAGE). The purified product was cleaved with PSP overnight, and the cleavage efficiency of GST-PF4 was approximately 100%. To improve the purification purity, the cleaved sample was purified using RESOURCE S (eluted with NaCl), and further purified using HiTrap Heparin HP (eluted with NaCl). As a result, 1.1 mL of 6.4 mg/mL PF4 (calculated from an absorbance at 280 nm (Abs280)) was obtained from *E. coli* corresponding to 3 L of the culture.

PF4 was denatured and reduced in the presence of 6 mol/L guanidine hydrochloride and 50 mmol/L DTT (dithiothreitol), and replaced with a denaturing solution composed of 8 mol/L urea and 5 mmol/L DTT. This denatured PF4 was concentrated to 10 mg/mL, and diluted 100 times with a refolding buffer containing 1 mmol/L oxidized glutathione and 10 mmol/L reduced glutathione at room temperature to carry out refolding. This refolding solution was applied to a heparin column, and PF4 was eluted using a linear concentration gradient of 0.3 to 2 mol/L NaCl in a 10 mmol/L sodium phosphate buffer (pH 7.5), and a heparin-high-affinity fraction eluted at 1.6 mol/L NaCl was fractionated. This fraction was used as recombinant PF4 in the subsequent experiments.

In accordance with a method disclosed in Heparin-induced Trombocytopenia (Marcel Dekker, Inc. New York, T. E. Warkentin et al), 470 µg/mL recombinant PF4 prepared as described above was mixed with 14 unit/mL heparin, sodium salt (from porcine intestinal mucosa, CALBIOCHEM) in a buffer of pH 7.5 at room temperature for 2 hours to prepare a heparin/PF4 complex.

Example 2

Preparation of Mouse Anti-Heparin/Pf4 Antibody

A 7-week-old female BALB/C mouse was immunized with the heparin/Pf4 complex prepared in Example 1 to prepare mouse anti-heparin/PF4 antibodies. More particularly, the heparin/Pf4 complex was diluted four times, and mixed with an equal amount of a Freund's complete adjuvant. The mouse was intracutaneously and intraperitoneally immunized with 500 µL of the mixture. This immunization was carried out in the same manner three times every 2 weeks, and hybridomas were prepared from spleen cells in accordance with a conventional method. The resulting hybridomas were screened by the ELISA method described in Example 5 to select 5 clones (10E6, 6G5-6H4, 5A1, 1G2B, and 2D6B) which reacted with the heparin/PF4 complex. The typing of each monoclonal antibody was determined in accordance with a conventional method to confirm that all the monoclonal antibodies were IgGκ. Each hybridoma was administered to the abdominal cavity of a mouse. After 2 weeks, the ascites were collected and applied to a protein G column to purify IgG, and anti-heparin/PF4 mouse monoclonal antibodies were obtained.

These 5 clones were examined in their reactivity to PF4 alone by the ELISA method described in Example 5, to confirm that all the monoclonal antibodies strongly reacted with PF4.

Example 3

Preparation of Hit Antibody Standard (Linkage of Human IgG to Mouse Anti-Heparin/PF4 Antibody)

To 0.5 mg of purified human IgG (1 mL, 50 mmol/L phosphate buffer, pH 7.0 containing 0.25 mol/L NaCl), which was commercially available, 21.3 µg of LC-SPDP (Succinimidyl 6-(3-[2-pyridyldithio]-propionamido)hexanoate, Pierce, 10 µL of dioxane) was added and reacted at room temperature for 1 hour with stirring. Next, 0.28 mL of 140 mmol/L dithiothreitol (distilled water) was added and allowed to stand at room temperature to carry out reduction. The reaction mixture was applied to a Sephadex G-25 column (1.5 cm×12 cm) equilibrated with a 50 mmol/L phosphate buffer, pH 7.0 containing 1 mmol/L EDTA, and the peak of the protein which was first eluted was collected by monitoring an absorbance at 280 nm.

To 0.5 mg of the anti-heparin/PF4 mouse monoclonal antibody prepared as above (clone 5A1, 1 mL, 50 mmol/L phosphate buffer, pH 7.0 containing 0.25 mol/L NaCl), 52 µg of SMCC (Succinimidyl-4-(N-maleimidomethyl)cyclohexane-1-carboxylate, Pierce, 30 µL of dimethylformamide) was added and reacted at room temperature for 1 hour with stirring. The reaction mixture was applied to a SEPHADEX® G-25 (cross-linked dextran gel) column (1.5 cm×12 cm) equilibrated with a 50 mmol/L phosphate buffer, pH 7.0 containing 1 mmol/L EDTA, and the peak of the protein which was first eluted was collected by monitoring an absorbance at 280 nm.

The human IgG into which SH groups had been introduced as above was mixed with an equal amount of the anti-heparin/PF4 mouse monoclonal antibody into which maleimide groups were introduced, and this mixture was allowed to stand at 4° C. overnight. As a blocker for excess maleimide groups, 10 µL, of 3 mg/mL 2-mercaptoethylamine (in distilled water) was added and allowed to stand at room temperature for 2 hours to carry out a reaction. The reaction product was fractionated by a SEPHACRYL® S-200 (composed of allyl dextran and N,N'-methylene bisacrylamide, cross-linked to form stable matrix) column (2.5×40 cm) equilibrated with a physiological saline, and the peak of a human-IgG-linked anti-heparin/PF4 mouse monoclonal antibody, which was eluted prior to the human anti-heparin/PF4 mouse monoclonal antibody, was collected.

The fractionation pattern of the gel filtration HPLC of the human-IgG-linked anti-heparin/PF4 mouse monoclonal antibody is shown in FIG. 1. The peak at an elution time of around 30 to 50 minutes was collected as the human-IgG-linked anti-heparin/PF4 mouse monoclonal antibody. It is considered that one or more human IgGs were linked to the anti-heparin/PF4 mouse monoclonal antibody.

The peak of an elution time of around 50 minutes was an unrelated excess human IgG, and the peak of an elution time of around 80 minutes was low molecular weight compounds such as an unrelated excess crosslinking agent (blocker).

Example 4

Preparation of Hit Antibody Standard (Linkage of Human IgG-Fc Fraction to Mouse Anti-Heparin/Pf4 Antibody)

One mg of a human IgG-Fc fraction (manufactured by BETHYL, catalogue No. P80-204, purchased from Cosmo Bio) was linked to 0.5 mg of each mouse anti-heparin/PF4 antibody (5A1, 2D6B, and 10E6) by repeating the procedures described in Example 3, except that the human IgG-Fc fraction was used instead of the human IgG, and that multiple antibody clones were used.

Figure 2:
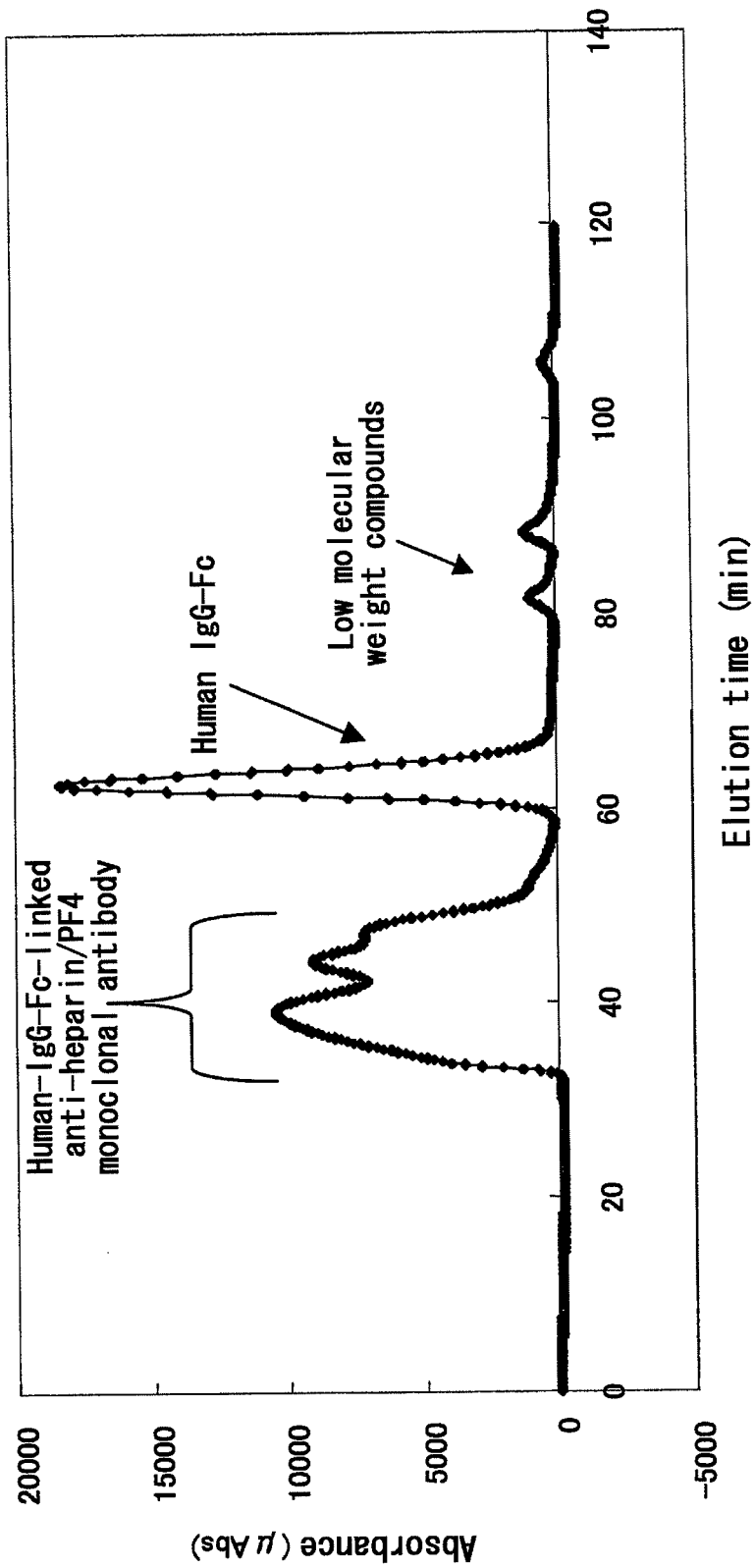
FIG. 2 is a chromatogram showing the fractionation pattern of a human-IgG-Fc-fraction-linked anti-heparin/PF4 mouse monoclonal antibody by gel filtration HPLC.

The fractionation pattern of the gel filtration HPLC of a human-IgG-Fc-fraction-linked mouse anti-heparin/PF4 antibody is shown in FIG. 2. The first peak at an elution time of around 30 to 50 minutes was collected as the human-IgG-Fc-fraction-linked anti-heparin/PF4 mouse monoclonal antibody. It is considered that one or more human IgG-Fc fractions were linked to the anti-heparin/PF4 mouse monoclonal antibody.

The peak at an elution time of around 60 minutes was an unrelated excess human IgG-Fc fraction, and the peak at an elution time of around 80 minutes was low molecular weight compounds such as an unrelated excess crosslinking agent (blocker).

Example 6

Confirmation of Reactivity of Hit Antibody Standard

The reactivity of the human-IgG-linked anti-heparin/PF4 mouse monoclonal antibody and the human-IgG-Fc-fraction-linked anti-heparin/PF4 mouse monoclonal antibodies which were prepared in Examples 3 and 4, respectively was confirmed as follows.

Into each well of an ELISA plate for physical adsorption (Coaster EIA/RIA plate, high binding 2592: manufactured by Coaster), 100 µL of 10 mmol/L PBS, pH 7.3, containing 1.2 µg of recombinant platelet factor 4 (PF4) prepared in Example 1 and 0.04 units of heparin (heparin, sodium salt, from porcine intestinal mucosa, manufactured by CALBIOCHEM) was poured, and allowed to stand at 4° C. overnight to coat the reaction wells. In addition, 100 µL of the buffer not containing heparin but containing PF4 was poured into some other wells, and allowed to stand at 4° C. overnight to coat the reaction wells.

Next, the reaction wells were washed with a washing liquid (PBS containing 0.1% Tween 20) three times, and each of the human-IgG-linked anti-heparin/PF4 mouse monoclonal antibody and the human-IgG-Fc-fraction-linked anti-heparin/PF4 mouse monoclonal antibodies, which were sequentially diluted with a diluent (PBS) containing 20% normal goat serum, was poured into the wells, and allowed to stand at room temperature for 1 hour to carry out a reaction.

After the wells were washed with the washing liquid three times, 100 μL of an anti-human-immunoglobulin antibody labeled with horseradish peroxidase (peroxidase-labeled and affinity-purified anti-human-immunoglobulin goat antibody F(ab')$_2$ fraction; manufactured by Jackson ImmunoResearch) diluted 3000-fold with the diluent was poured into the wells, and allowed to stand at room temperature for 1 hour to carry out a reaction. Next, the wells were washed with the washing liquid four times, and 100 μL of a developing liquid (50 mmol/L acetate buffer, pH5.5 containing 0.006% hydrogen peroxide and 2 mg of o-phenylenediamine) was poured into the wells, and reacted at room temperature for 10 minutes. Then, 100 μL of a stopping liquid (0.5 mol/L sulfuric acid) was added, and the degree of development was measured using an ELISA plate reader (microplate reader MPR-A4i; Toso Co., Ltd.) equipped with a filter having a main wavelength of 492 nm and a sub wavelength of 620 nm.

Figure 3:
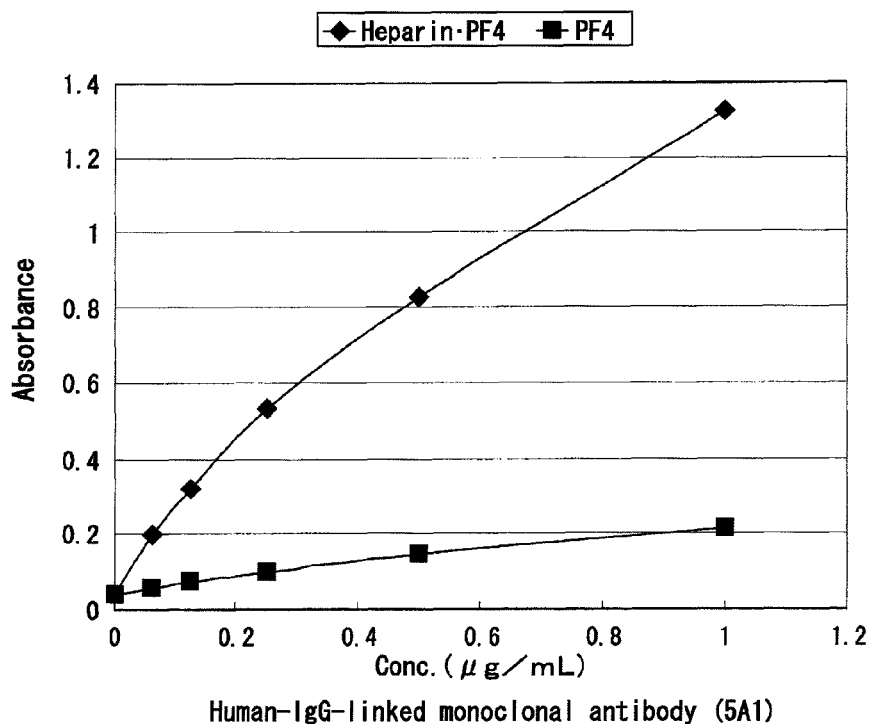
FIG. 3 is a graph showing the reactivity of a human-IgG-linked anti-heparin/PF4 mouse monoclonal antibody (5A1) against a heparin/Pf4 complex plate or a PF4 plate.
Figure 4:
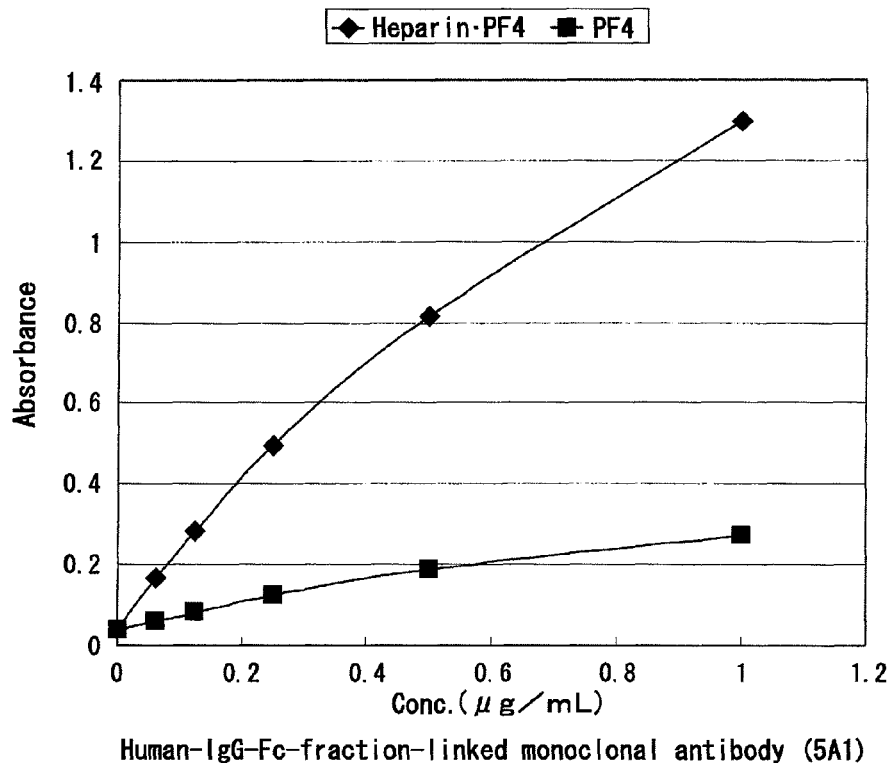
FIG. 4 is a graph showing the reactivity of a human-IgG-Fc-fraction-linked anti-heparin/PF4 mouse monoclonal antibody (5A1) against a heparin/Pf4 complex plate or a PF4 plate.
Figure 5:
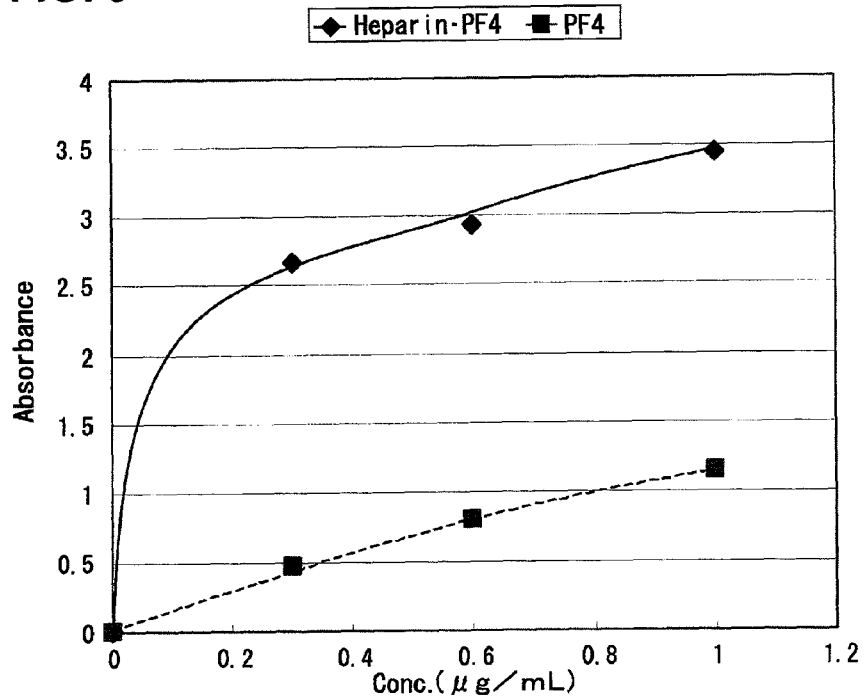
FIG. 5 is a graph showing the reactivity of a human-IgG-Fc-fraction-linked anti-heparin/PF4 mouse monoclonal antibody (2D6B) against a heparin/Pf4 complex plate or a PF4 plate.
Figure 6:
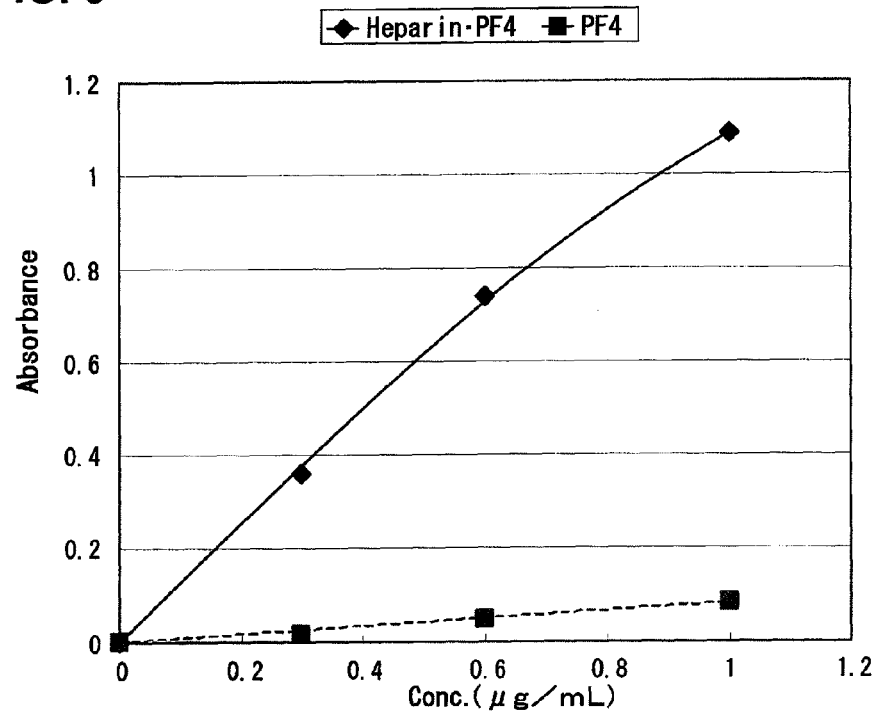
FIG. 6 is a graph showing the reactivity of a human-IgG-Fc-fraction-linked anti-heparin/PF4 mouse monoclonal antibody (10E6) against a heparin/Pf4 complex plate or a PF4 plate.

The reactivity of the human-IgG-linked anti-heparin/PF4 mouse monoclonal antibody against the plate coated with the heparin/PF4 complex (heparin/PF4 complex plate) or the plate coated with PF4 (PF4 plate) is shown in FIG. 3. The reactivity of each of the human-IgG-Fc-fraction-linked anti-heparin/PF4 mouse monoclonal antibodies against the heparin/PF4 complex plate or the PF4 plate is shown in FIG. 4 (5A1), FIG. 5 (2D6B), and FIG. 6 (10E6).

Figure 7:
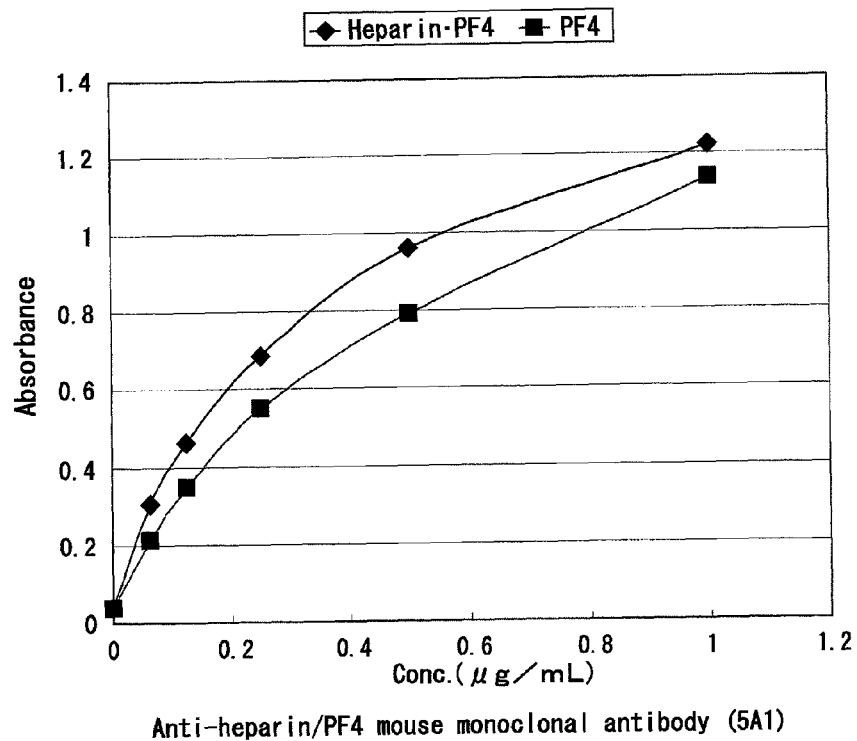
FIG. 7 is a graph showing the reactivity of an anti-heparin/PF4 mouse monoclonal antibody (5A1) against a heparin/Pf4 complex plate or a PF4 plate.
Figure 8:
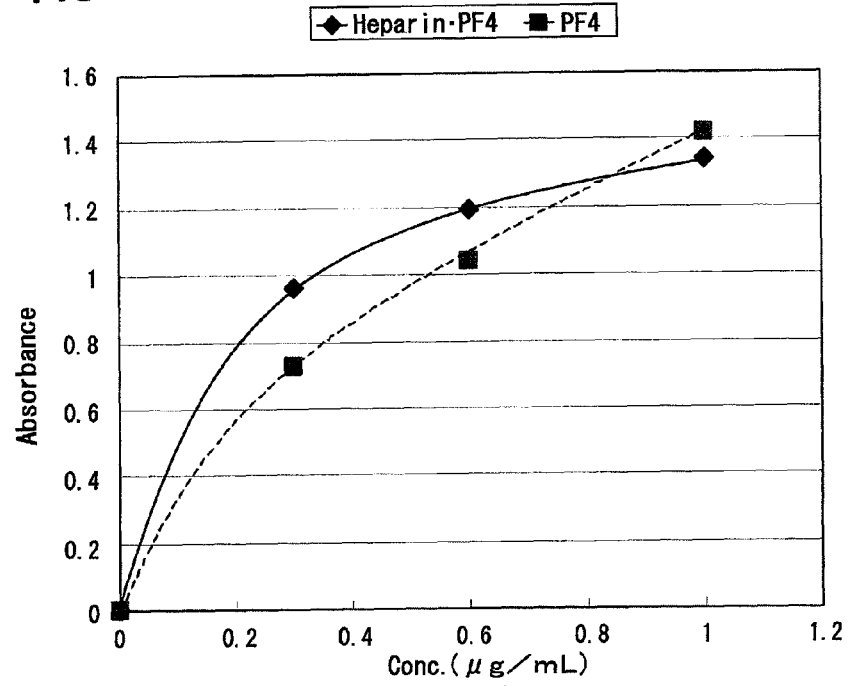
FIG. 8 is a graph showing the reactivity of an anti-heparin/PF4 mouse monoclonal antibody (2D6B) against a heparin/Pf4 complex plate or a PF4 plate.
Figure 9:
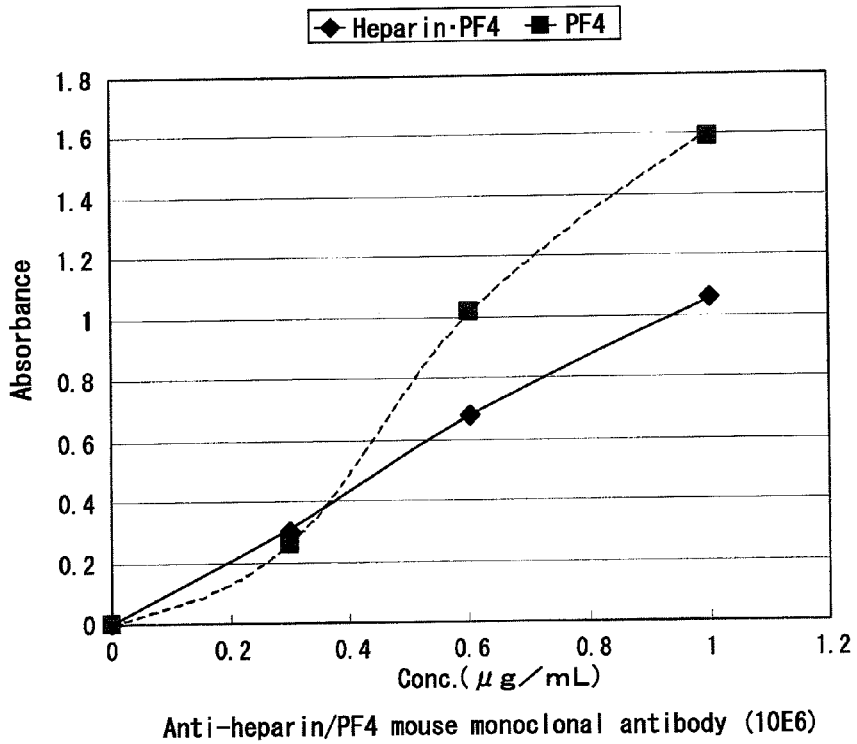
FIG. 9 is a graph showing the reactivity of an anti-heparin/PF4 mouse monoclonal antibody (10E6) against a heparin/Pf4 complex plate or a PF4 plate.

As negative controls, the reactivity of each of the anti-heparin/PF4 mouse monoclonal antibodies against the heparin/PF4 complex plate or the PF4 plate was examined in a similar fashion. Because the anti-heparin/PF4 mouse monoclonal antibodies do not have a human IgG component, an anti-mouse-immunoglobulin antibody labeled with HRP (horseradish peroxidase-labeled anti-mouse-immunoglobulin rabbit IgG antibody; manufactured by DAKO) was used as the labeling antibody. The results are shown in FIG. 7 (5A1), FIG. 8 (2D6B), and FIG. 9 (10E6).

With respect to all of the anti-heparin/PF4 mouse monoclonal antibodies, linkage to the human IgG component could provide modified antibodies that hardly reacted with PF4 alone, but strongly reacted with the heparin/PF4 complex, like a human autoantibody (HIT antibody).

Therefore, it was confirmed that these modified antibodies (the human-IgG-linked anti-heparin/PF4 mouse monoclonal antibody and the human-IgG-Fc-fraction-linked anti-heparin/PF4 mouse monoclonal antibodies) could be used as an HIT antibody standard for measuring the HIT antibody contained in human samples.

Example 6

Measurement and Quantification of Hit Antibody Contained in Human Samples

Figure 10:
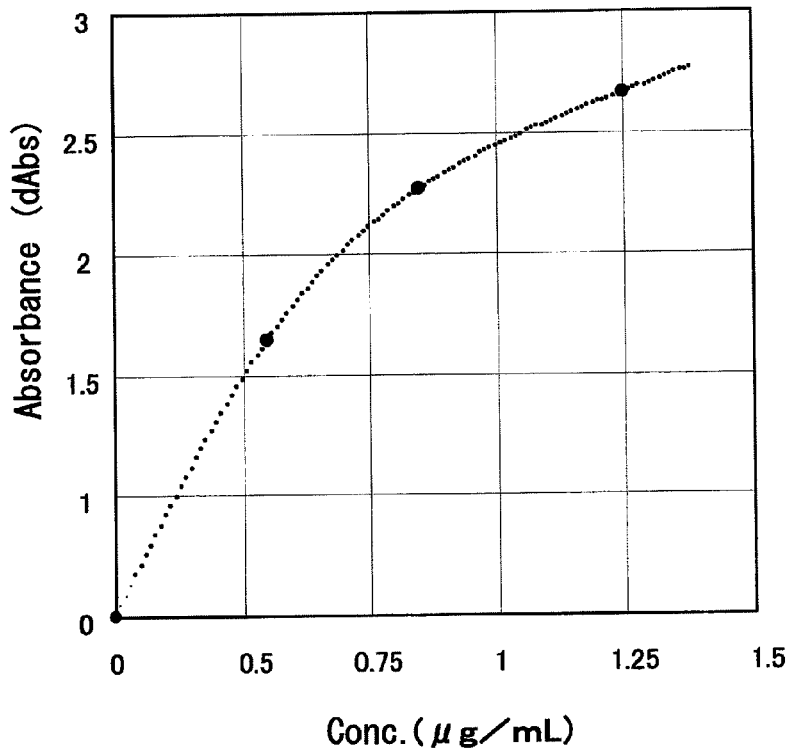
FIG. 10 is a graph showing a standard curve drawn using the HIT antibody standard of the present invention.

To quantify the HIT antibody contained in human samples, a standard curve was prepared using the HIT antibody standard prepared above (human-IgG-Fc-fraction-linked anti-heparin/PF4 mouse monoclonal antibody (5A1)). This HIT antibody standard corresponds to 2 units per 1 μg/mL. The HIT antibody standard was diluted to 0, 0.3, 0.6, and 1 μg/mL (corresponding to 0, 0.6, 1.2, and 2 units, respectively), the reactivity against the heparin/PF4 complex plate was measured in a similar fashion to that described in Example 5. The OD values were 0.005, 1.140, 1.743, and 2.191, respectively. From these values, a standard curve was prepared using a spline approximation. The result is shown in FIG. 10. It was found that a standard curve which passed through the four points obtained could be drawn.

Actual samples (80 samples) were diluted by 101-fold, and the reactivity against the heparin/PF4 complex plate was measured in a similar fashion to that described in Example 5. The obtained OD values and the standard curve prepared above were used to calculate each concentration (μg/mL). The result is shown in Table 1. With respect to all samples, the concentration of the HIT antibody contained in each sample could be determined from the standard curve.

TABLE 1

| Sample No. | Dia-1 | Dia-2 | Dia-3 | Dia-4 | Dia-5 | Dia-6 | Dia-7 | Dia-8 | Dia-9 | Dia-10 |
|---|---|---|---|---|---|---|---|---|---|---|
| OD value | 0.138 | 0.211 | 0.173 | 0.167 | 0.301 | 0.275 | 0.203 | 0.233 | 0.225 | 0.143 |
| Conc. | 0.032 | 0.049 | 0.040 | 0.039 | 0.071 | 0.065 | 0.047 | 0.054 | 0.053 | 0.033 |
| Sample No. | Dia-11 | Dia-12 | Dia-13 | Dia-14 | Dia-15 | Dia-16 | Dia-17 | Dia-18 | Dia-19 | Dia-20 |
| OD value | 0.144 | 0.146 | 0.184 | 0.192 | 0.177 | 0.142 | 0.151 | 0.172 | 0.218 | 0.156 |
| Conc. | 0.033 | 0.034 | 0.043 | 0.045 | 0.041 | 0.033 | 0.035 | 0.040 | 0.051 | 0.036 |
| Sample No. | Dia-21 | Dia-22 | Dia-23 | Dia-24 | Dia-25 | Dia-26 | Dia-27 | Dia-29 | Dia-29 | Dia-30 |
| OD value | 0.185 | 0.244 | 0.207 | 0.292 | 0.210 | 0.221 | 0.198 | 0.564 | 0.109 | 0.183 |
| Conc. | 0.043 | 0.057 | 0.048 | 0.069 | 0.049 | 0.052 | 0.046 | 0.136 | 0.025 | 0.042 |
| Sample No. | Dia-31 | Dia-32 | Dia-33 | Dia-34 | Dia-35 | Dia-36 | Dia-37 | Dia-38 | Dia-39 | Dia-40 |
| OD value | 0.185 | 0.169 | 0.246 | 0.230 | 0.107 | 0.110 | 0.163 | 0.879 | 0.631 | 0.771 |
| Conc. | 0.043 | 0.039 | 0.058 | 0.054 | 0.024 | 0.025 | 0.038 | 0.220 | 0.153 | 0.190 |
| Sample No. | Dia-41 | Dia-42 | Dia-43 | Dia-44 | Dia-45 | Dia-46 | Dia-47 | Dia-48 | Dia-49 | Dia-50 |
| OD value | 0.163 | 0.158 | 0.127 | 0.172 | 0.169 | 0.075 | 0.135 | 0.163 | 0.145 | 0.210 |
| Conc. | 0.038 | 0.036 | 0.029 | 0.040 | 0.039 | 0.017 | 0.031 | 0.038 | 0.033 | 0.049 |

TABLE 1-continued

| Sample No. | Dia-51 | Dia-52 | Dia-53 | Dia-54 | Dia-55 | Dia-56 | Dia-57 | Dia-58 | Dia-59 | Dia-60 |
|---|---|---|---|---|---|---|---|---|---|---|
| OD value | 0.190 | 0.224 | 0.130 | 0.126 | 0.133 | 0.102 | 0.104 | 0.134 | 0.129 | 0.154 |
| Conc. | 0.044 | 0.052 | 0.030 | 0.029 | 0.030 | 0.023 | 0.024 | 0.031 | 0.030 | 0.036 |
| Sample No. | Dia-61 | Dia-62 | Dia-63 | Dia-64 | Dia-65 | Dia-66 | Dia-67 | Dia-68 | Dia-69 | Dia-70 |
| OD value | 0.167 | 0.292 | 0.299 | 0.901 | 0.313 | 0.357 | 0.507 | 0.187 | 0.191 | 0.387 |
| Conc. | 0.039 | 0.069 | 0.070 | 0.226 | 0.074 | 0.084 | 0.121 | 0.043 | 0.044 | 0.092 |
| Sample No. | Dia-71 | Dia-72 | Dia-73 | Dia-74 | Dia-75 | Dia-76 | Dia-77 | Dia-78 | Dia-79 | Dia-80 |
| OD value | 0.446 | 2.734 | 2.435 | 0.091 | 0.125 | 0.341 | 0.485 | 0.119 | 0.150 | 0.158 |
| Conc. | 0.106 | 1.551 | 1.248 | 0.020 | 0.029 | 0.081 | 0.116 | 0.027 | 0.035 | 0.036 |

INDUSTRIAL APPLICABILITY

The modified antibody of the present invention can be applied to an analysis of the heparin/PF4 complex, which is an onset factor of HIT. The modified antibody of the present invention can be used as an HIT antibody standard.

Although the present invention has been described with reference to specific embodiments, various changes and modifications obvious to those skilled in the art are possible without departing from the scope of the appended claims.

The invention claimed is:

1. A modified anti-heparin/platelet factor 4 (PF4) complex antibody, comprising (i) a human IgG or its Fc fraction and (ii) an original monoclonal antibody obtained by immunizing a non-human animal with a heparin/PF4 complex, said human IgG or IgG Fe fraction being linked to the original monoclonal antibody,
   wherein the original monoclonal antibody shows substantially the same reactivities against the heparin/PF4 complex and PF4, and
   the modified anti-heparin/PF4 complex antibody reacts with the heparin/PF4 complex, but does not react with FF4.

2. A heparin-induced thrombocytopenia (HIT) antibody standard, comprising (i) a human IgG or its Fe fraction, and (ii) an original monoclonal antibody obtained by immunizing a non-human animal with a heparin/PF4 complex, said human IgG or antibody fragment being linked to the original monoclonal antibody,
   wherein the original monoclonal antibody shows substantially the same reactivities against the heparin/PF4 complex and PF4, and
   the HIT antibody standard reacts with the heparin/PF4 complex, but does not react with PF4.

3. A process of preparing an HIT antibody standard, comprising linking a human IgG or its Fc fraction to an original monoclonal antibody obtained by immunizing a non-human animal with a heparin/PF4 complex,
   wherein the original monoclonal antibody shows substantially the same reactivities against the heparin/PF4 complex and PF4, and
   the HIT antibody standard reacts with the heparin/PF4 complex, but does not react with PF4.

4. A method of quantitatively measuring an HIT antibody contained in a sample, comprising the steps of:
   contacting the sample with immobilized heparin/PF4 complex and measuring binding of HIT antibody in the sample to the immobilized heparin/PF4 complex so as to obtain a measured value of the HIT antibody in the sample;
   drawing a standard curve using the HIT antibody standard of claim 2, and
   determining the concentration of the HIT antibody contained in the sample from the measured value of the HIT antibody in the sample using the standard curve.

5. A kit for measuring a HIT antibody, comprising the HIT antibody standard of claim 2.

* * * * *